(12) United States Patent
Choi et al.

(10) Patent No.: US 10,610,441 B2
(45) Date of Patent: Apr. 7, 2020

(54) JOINT ASSEMBLY AND MOTION ASSISTANCE APPARATUS INCLUDING THE SAME

(71) Applicant: Samsung Electronics Co., Ltd., Suwon-si, Gyeonggi-do (KR)

(72) Inventors: Byungjune Choi, Gunpo-si (KR); Younbaek Lee, Yongin-si (KR); Jongwon Lee, Suwon-si (KR); Jeonghun Kim, Suwon-si (KR); Se-Gon Roh, Suwon-si (KR); Minhyung Lee, Seoul (KR); Jungyun Choi, Seoul (KR); Hyun Do Choi, Yongin-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 238 days.

(21) Appl. No.: 15/604,891

(22) Filed: May 25, 2017

(65) Prior Publication Data

US 2018/0161229 A1    Jun. 14, 2018

(30) Foreign Application Priority Data

Dec. 9, 2016 (KR) .................. 10-2016-0167863

(51) Int. Cl.
*A61H 3/00* (2006.01)
*A61F 5/01* (2006.01)
*A61F 2/50* (2006.01)
*B25J 9/00* (2006.01)

(52) U.S. Cl.
CPC ............ *A61H 3/00* (2013.01); *A61F 2/50* (2013.01); *A61F 5/0123* (2013.01); *B25J 9/0006* (2013.01); *A61F 2002/5007* (2013.01); *A61F 2002/5038* (2013.01); *A61F 2005/0137* (2013.01); *A61F 2005/0139* (2013.01); *A61F 2005/0141* (2013.01); *A61F 2005/0155* (2013.01)

(58) Field of Classification Search
CPC ........................................ A61F 5/01
See application file for complete search history.

(56) References Cited

U.S. PATENT DOCUMENTS

| | | | |
|---|---|---|---|
| 5,178,137 A | 1/1993 | Goor et al. |
| 5,261,871 A | 11/1993 | Greenfield |
| 7,806,842 B2 | 10/2010 | Stevenson et al. |
| 9,333,107 B2 | 5/2016 | Potter et al. |
| 2012/0330198 A1 | 12/2012 | Patoglu |

(Continued)

FOREIGN PATENT DOCUMENTS

| | | |
|---|---|---|
| DE | 42 22 601 A1 | 1/1994 |
| JP | 2010-082342 A | 4/2010 |

(Continued)

OTHER PUBLICATIONS

Extended European Search Report dated Feb. 27, 2018 for corresponding EP Application No. 17179356.5.

*Primary Examiner* — Yashita Sharma
(74) *Attorney, Agent, or Firm* — Harness, Dickey & Pierce, P.L.C.

(57) ABSTRACT

A joint assembly may include a first rolling cam that includes a first cam portion, and a first extension extending from the first cam portion, and a second rolling cam that includes a second cam portion to be in contact with the first cam portion, and a second extension extending from the second cam portion.

18 Claims, 21 Drawing Sheets

(56) References Cited

U.S. PATENT DOCUMENTS

2014/0148747 A1 5/2014 Fleming
2015/0051527 A1 2/2015 Potter et al.
2015/0366696 A1 12/2015 Ingimundarson et al.

FOREIGN PATENT DOCUMENTS

JP 2015123563 A 7/2015
WO WO-2015/157731 A1 10/2015

JOINT ASSEMBLY AND MOTION ASSISTANCE APPARATUS INCLUDING THE SAME

CROSS-REFERENCE TO RELATED APPLICATION

This application claims under 35 U.S.C. § 119 to Korean Patent Application No. 10-2016-0167863, filed on Dec. 9, 2016, in the Korean Intellectual Property Office, the entire contents of which are incorporated herein by reference in their entirety.

BACKGROUND

1. Field

At least one example embodiment relates to a joint assembly and/or a motion assistance apparatus including the same.

2. Description of the Related Art

Motion assistance apparatuses enabling the elderly and/or patients having joint problems to walk with less effort, and motion assistance apparatuses increasing muscular strength of users for military purposes are being developed.

SUMMARY

Some example embodiments relate to a joint assembly.

In some example embodiment, the joint assembly may include a first rolling cam including a first cam portion, and a first extension, the first extension extending from the first cam portion; and a second rolling cam including a second cam portion and a second extension, the second cam portion configured to contact the first cam portion and the second extension extending from the second cam portion.

In some example embodiment, the first cam portion has a shape symmetrical in a lateral direction with respect to a first virtual center line, and the second cam portion has a shape symmetrical in a lateral direction with respect to a second virtual center line.

In some example embodiment, an edge shape of the first cam portion and an edge shape of the second cam portion satisfy Equation 1 and Equation 2, respectively, $$r1 = \frac{C(\phi)}{2}, \theta1 = \frac{\phi}{2}$$ [Equation 1]

$$r2 = \frac{C(\phi)}{2}, \theta2 = \frac{\phi}{2},$$ [Equation 2]

wherein $\phi$ denotes an angle between the first virtual center line and the second virtual center line, $C(\phi)$ denotes a distance between the first virtual center line and the second virtual center line in a direction orthogonal to a tangent line at a point at which the first cam portion is in contact with the second cam portion, r1 denotes a distance from a first intersection point to a point on an edge of the first cam portion, the first intersection point being a point at which the first virtual center line and a first orthogonal virtual line orthogonal thereto meet, $\theta1$ denotes an angle measured in a clockwise direction from a positive direction of the first orthogonal virtual line to a virtual line connecting the first intersection point and the point on the edge of the first cam portion, r2 denotes a distance from a second intersection point to a point on an edge of the second cam portion, the second intersection point being a portion at which the second virtual center line and a second orthogonal virtual line orthogonal thereto meet, and $\theta2$ denotes an angle measured in a counterclockwise direction from a negative of the second orthogonal virtual line to a virtual line connecting the second intersection point and the point on the edge of the second cam portion.

In some example embodiment, a width of the first extension decreases in a direction away from the first cam portion.

In some example embodiment, the first rolling cam further includes a rotary member associated with the first extension, the rotary member configured to rotate.

In some example embodiment, the rotary member is exposed outside of the first extension.

In some example embodiment, the joint assembly may further include a rolling cam guide configured to cover at least a portion of a side of the first rolling cam and at least a portion of a side of the second rolling cam.

In some example embodiment, the joint assembly may further include a rolling cam guide including a fixed portion and a guide portion, the fixed portion configured to attach to a side of the first rolling cam, and the guide portion extending from the fixed portion and overlapping at least a portion of a side of the second rolling cam.

In some example embodiment, the joint assembly may further include a slip reducer between the first cam portion and the second cam portion.

In some example embodiment, the joint assembly may further include an elastic member between the first rolling cam and the second rolling cam.

In some example embodiment, the joint assembly may further include a first longitudinal member connecting the first cam portion and the second cam portion; and a second longitudinal member connecting the first extension and the second extension.

In some example embodiment, a sum of a product of an angle $\phi$ and a distance d and an initial distance C0 is equal to a length of a portion between a point of the first extension connected to the second longitudinal member and a point of the second extension connected to the second longitudinal member, the angle $\phi$ is an angle between the first rolling cam and the second rolling cam, the distance d is a distance from a cam center of the second cam portion to the point of the second extension connected to the second longitudinal member, and the initial distance C0 is a distance between a cam center of the first cam portion and the cam center of the second cam portion when the angle $\phi$ corresponds to 0 degrees.

Other example embodiments relate to a motion assistance apparatus.

In some example embodiments, the motion assistance apparatus may include a first support configured to support a first portion of a user; a second support configured to support a second portion of the user; and a first joint assembly including a plurality of first rolling cams and at least one longitudinal member configured to bind the plurality of rolling cams, the plurality of first rolling cams being between the first support and the second support.

In some example embodiment, each of the plurality of first rolling cams may include a cam portion; and an extension extending from the cam portion.

In some example embodiment, the at least one longitudinal member includes a first longitudinal member connected to the cam portion of each of the plurality of first rolling cams; and a second longitudinal member connected to the extension of each of the plurality of first rolling cams.

In some example embodiment, the motion assistance apparatus may further include a second joint assembly including a plurality of second rolling cams configured to connect the first support and the second support, wherein the first joint assembly is configured to attach to an outer side of the user, and the second joint assembly is configured to attach to an inner side of the user.

In some example embodiment, the motion assistance apparatus may further include a first pulley configured to rotate with respect to the second support, the first pulley configured to hold a central portion of the first longitudinal member, the first longitudinal member being connected to the outer side of the user and the inner side of the user.

In some example embodiment, the motion assistance apparatus may further include a second pulley configured to rotate with respect to the second support, the second pulley configured to hold a central portion of the second longitudinal member, the second longitudinal member being connected to the outer side of the user and the inner side of the user.

In some example embodiment, the first support may include a first supporting frame configured to enclose the first portion of the user; and a rotor configured to rotate with respect to the first supporting frame, the rotor configured to connect to a first end portion of the first longitudinal member and a first end portion of the second longitudinal member.

In some example embodiment, the rotor may include a rotor body configured to rotate with respect to the first support; and a tensile force adjuster movably provided in the rotor body, the tensile force adjustor configured to connect to one end of one of the first longitudinal member and the second longitudinal member.

In some example embodiment, the motion assistance apparatus may further include a slack reducing elastic body connected to a second end portion of the first longitudinal member and a second end portion of the second longitudinal member.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects will become apparent and more readily appreciated from the following description of example embodiments, taken in conjunction with the accompanying drawings of which.

DETAILED DESCRIPTION

Figure 1:
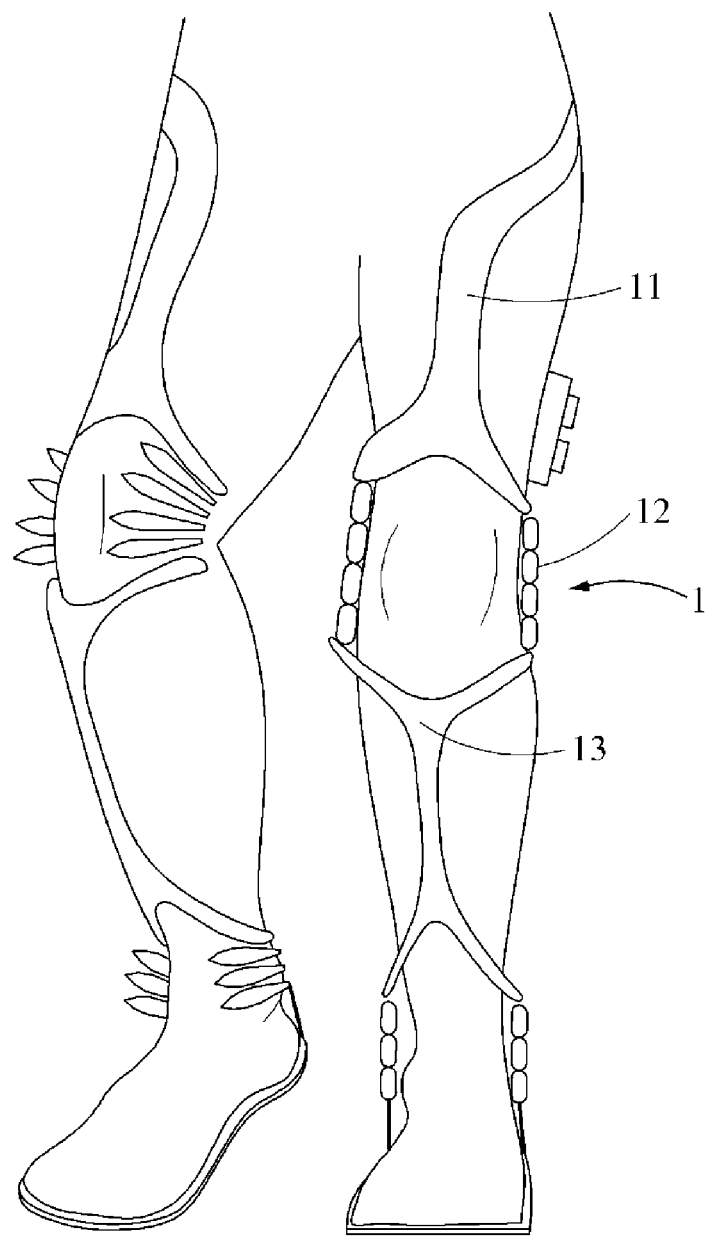
FIG. 1 is a perspective view illustrating a motion assistance apparatus according to at least one example embodiment.

Hereinafter, some example embodiments will be described in detail with reference to the accompanying drawings. Regarding the reference numerals assigned to the elements in the drawings, it should be noted that the same elements will be designated by the same reference numerals, wherever possible, even though they are shown in different drawings. Also, in the description of embodiments, detailed description of well-known related structures or functions will be omitted when it is deemed that such description will cause ambiguous interpretation of the present disclosure.

It should be understood, however, that there is no intent to limit this disclosure to the particular example embodiments disclosed. On the contrary, example embodiments are to cover all modifications, equivalents, and alternatives falling within the scope of the example embodiments. Like numbers refer to like elements throughout the description of the figures.

In addition, terms such as first, second, A, B, (a), (b), and the like may be used herein to describe components. Each of these terminologies is not used to define an essence, order or sequence of a corresponding component but used merely to distinguish the corresponding component from other component(s). It should be noted that if it is described in the specification that one component is "connected", "coupled", or "joined" to another component, a third component may be "connected", "coupled", and "joined" between the first and second components, although the first component may be directly connected, coupled or joined to the second component.

The terminology used herein is for the purpose of describing particular embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Figure 2:
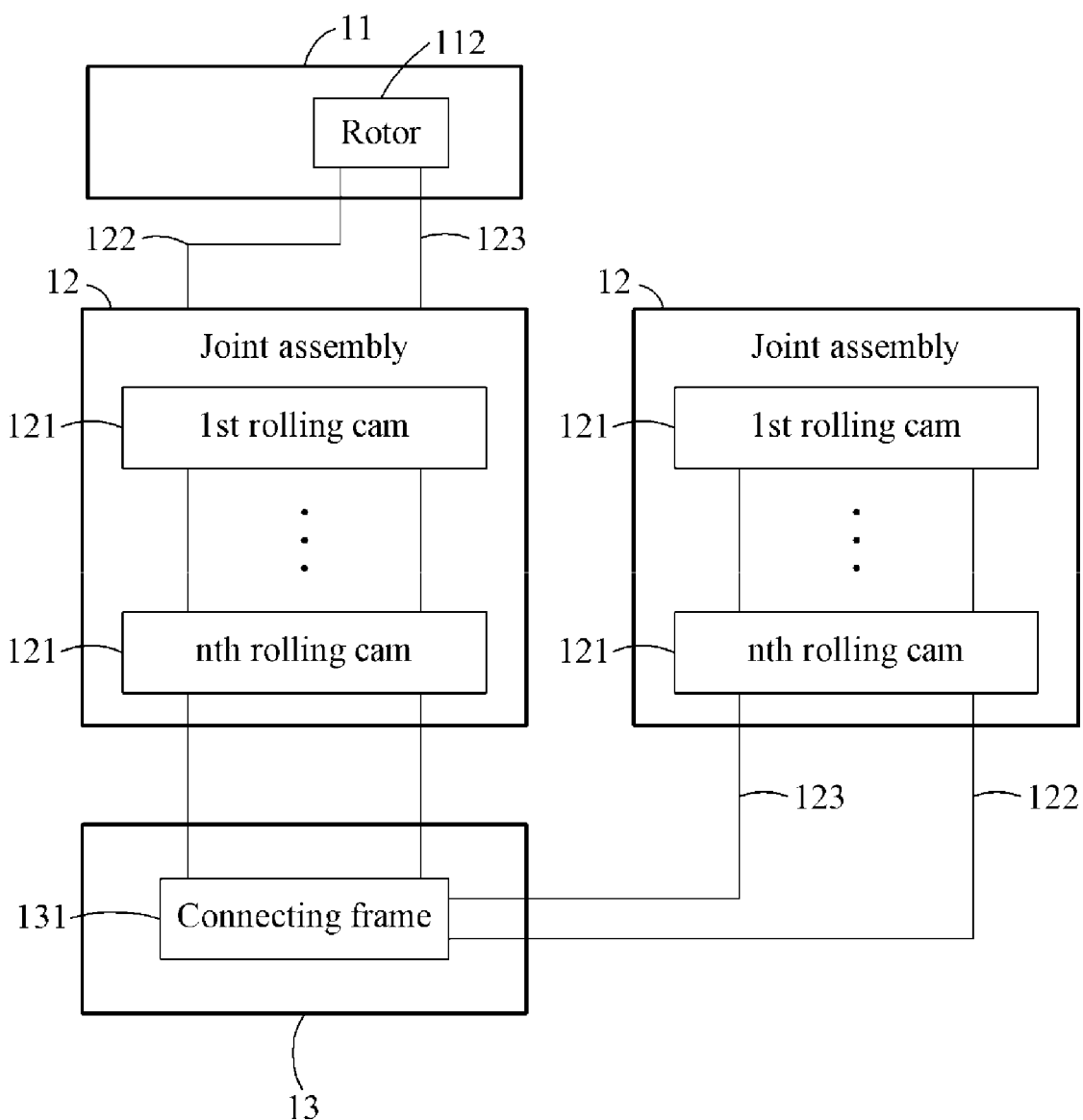
FIG. 2 is a block diagram illustrating a motion assistance apparatus according to at least one example embodiment.

FIG. 1 is a perspective view illustrating a motion assistance apparatus according to at least one example embodiment, and FIG. 2 is a block diagram illustrating the motion assistance apparatus according to at least one example embodiment.

Figure 3:
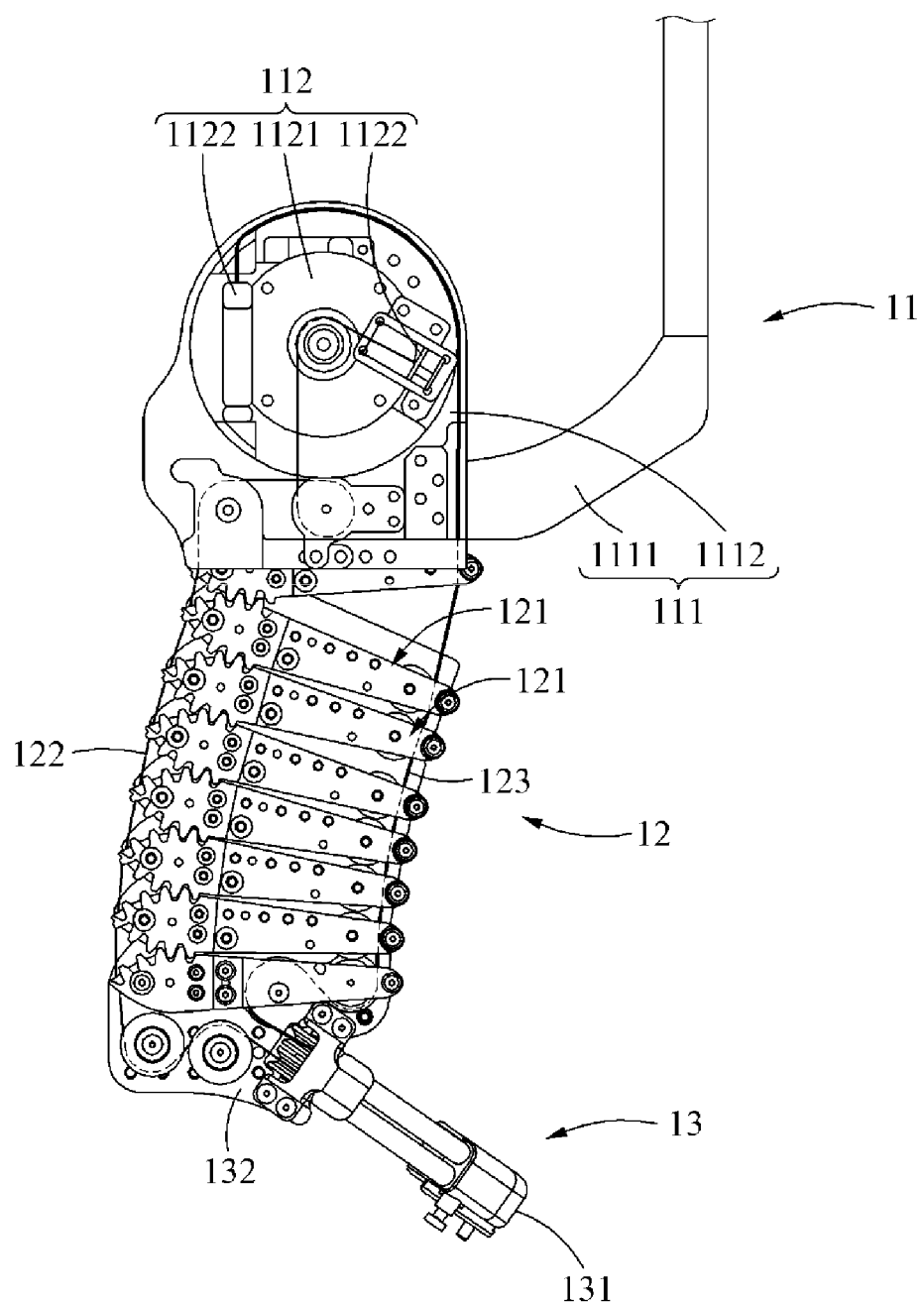
FIG. 3 is a side view illustrating a motion assistance apparatus according to at least one example embodiment.
Figure 4:
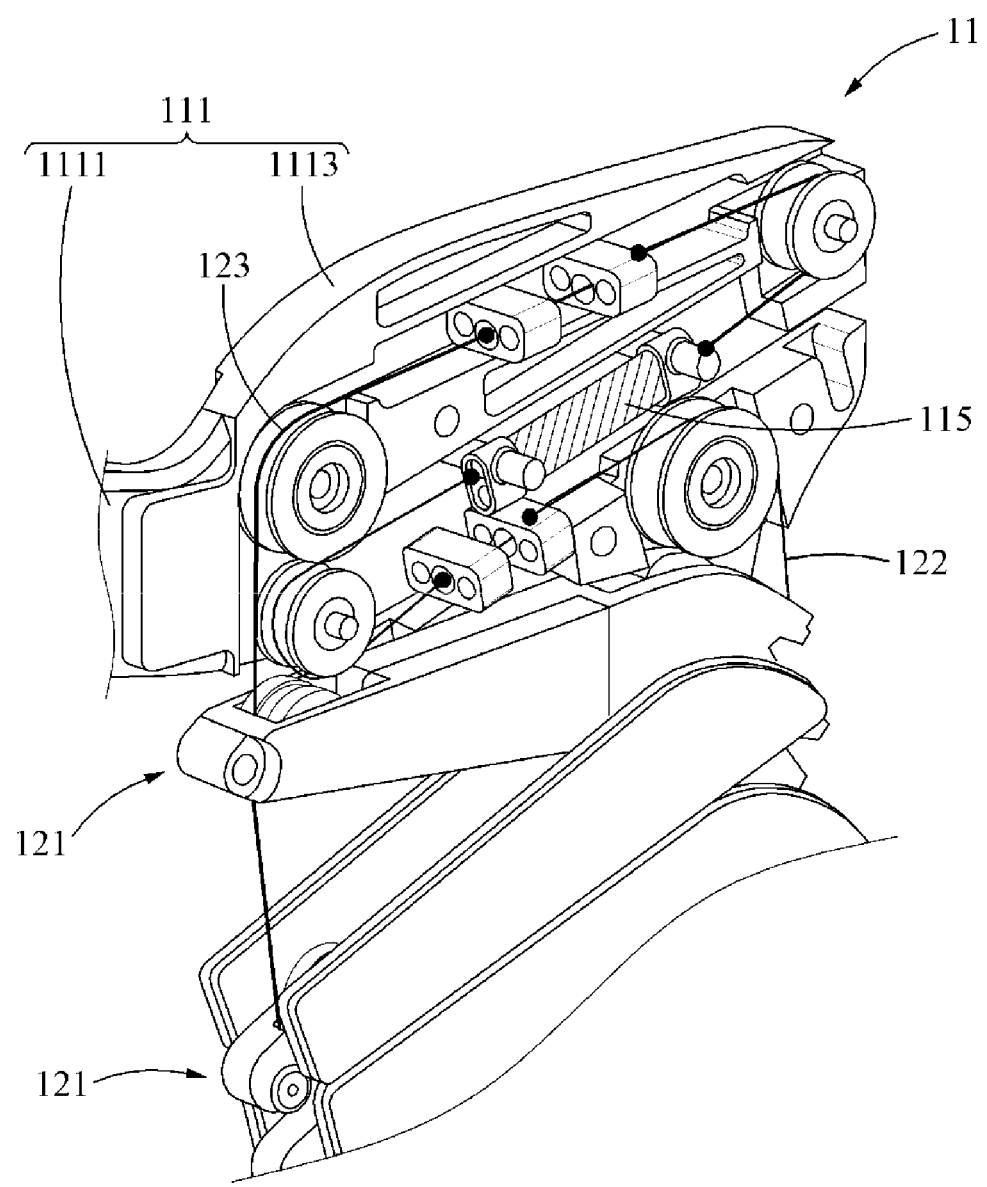
FIG. 4 is a perspective view enlarging a portion of a first support according to at least one example embodiment.
Figure 5:
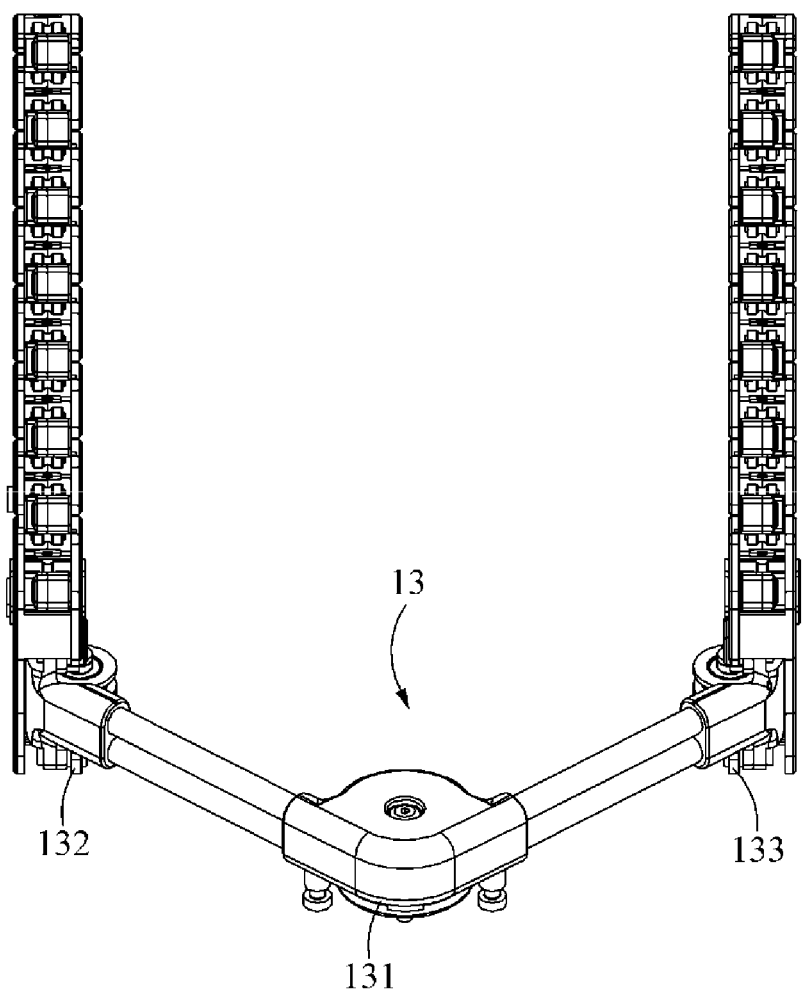
FIG. 5 is a front view illustrating a second support according to at least one example embodiment.
Figure 6:
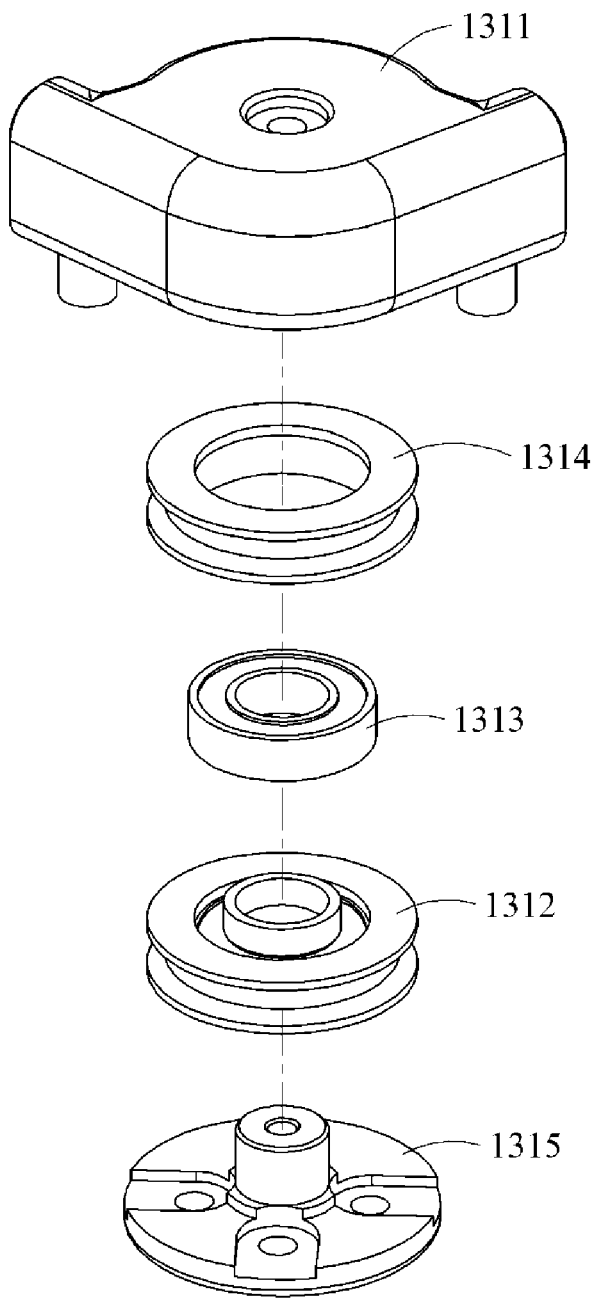
FIG. 6 is an exploded perspective view enlarging a portion of a second support according to at least one example embodiment.

FIG. 3 is a side view illustrating the motion assistance apparatus according to at least one example embodiment, FIG. 4 is a perspective view enlarging a portion of a first support according to at least one example embodiment, FIG. 5 is a front view illustrating a second support according to at least one example embodiment, and FIG. 6 is an exploded perspective view enlarging a portion of the second support according to at least one example embodiment.

Referring to FIGS. 1 through 6, a motion assistance apparatus 1 may be worn by a user to assist a motion of the user. The user may correspond to a human, an animal, or a robot. However, the user is not limited thereto. Although FIG. 1 illustrates a case in which the motion assistance apparatus 1 assist a motion of a knee joint of the user, the motion assistance apparatus 1 may also assist a motion of another portion of the user, for example, a wrist joint, an elbow joint, or an ankle joint. That is, the motion assistance apparatus 1 may assist a motion of a portion of the user. Hereinafter, a case in which the motion assistance apparatus 1 assists a motion of a knee joint of a human will be described.

The motion assistance apparatus 1 may include a joint assembly 12, a first support 11 connected to one side of the joint assembly 12, and a second support 13 connected to another side of the joint assembly 12.

The first support 11 may include a first supporting frame 111, a rotor 112, and a slack preventing elastic body 115.

The first supporting frame 111 may support a first portion of the user, and be provided in a shape that encloses the first portion along an outer surface of the user. For example, the first supporting frame 111 may be provided to enclose a thigh of the user, and provided in a shape including a side corresponding to a contact portion of the user. The first supporting frame 111 may include a connecting frame 1111, a first outer side frame 1112 disposed on an outer side of the thigh, and a first inner side frame 1113 disposed on an inner side of the thigh. The connecting frame 1111 may be configured to connect the first outer side frame 1112 and the first inner side frame 1113.

The rotor 112 may be rotatably provided in the first supporting frame 111, for example, the first outer side frame 1112. The rotor 112 may implement a flexion motion or extension motion of the joint assembly 12 based on a rotating direction. A first longitudinal member 122 and a second longitudinal member 123 of the joint assembly 12 may be connected to the rotor 112. For example, the rotor 112 may be a pulley to be used to pull or release the first longitudinal member 122 and the second longitudinal member 123. The rotor 112 may include a rotor body 1121 configured to rotate with respect to the first supporting frame 111, and a tensile force adjuster 1122.

The tensile force adjuster 1122 may be fixed to one end of one of the first longitudinal member 122 and the second longitudinal member 123, and move relative to the rotor 112. In the above structure, although the first longitudinal member 122 or the second longitudinal member 123 is loosened as the user repeatedly uses the motion assistance apparatus 1, the tensile force adjuster 1122 may be used to control the first longitudinal member 122 or the second longitudinal member 123 to have a desired tensile force. The tensile force adjuster 1122 may be detachably connected to the rotor 112. In the above structure, the first longitudinal member 122 or the second longitudinal member 123 may be easily separated from the motion assistance apparatus 1 for replacement.

The slack preventing elastic body 115 may be disposed in the first supporting frame 111, for example, the first inner side frame 1113. The first longitudinal member 122 and the second longitudinal member 123 may be connected to the slack preventing elastic body 115. For example, the slack preventing elastic body 115 may be an elastic body such as a spring or a rubber band that has elasticity. The slack preventing elastic body 115 may reduce (or, alternatively, prevent) slack. Slack may be a phenomenon that the second longitudinal member 123 connected to the rotor 112 is released and loosened when the first longitudinal member 122 connected to the rotor 112 is pulled. That is, the slack preventing elastic body 115 may pull the first longitudinal member 122 and/or the second longitudinal member 123 using an elastic force to compensate for looseness in a case in which one longitudinal member is loosened when the other longitudinal member is pulled or released.

The joint assembly 12 may include a plurality of rolling cams 121 disposed between the first support 11 and the second support 13, and at least one longitudinal member 122, 123 configured to bind the plurality of rolling cams 121. For example, in a case in which the joint assembly 12 includes two longitudinal members 122 and 123, bidirectional actuation of the joint assembly 12, that is, actuation in directions of flexion motion and extension motion, may be enabled by pulling one of the two longitudinal members 122 and 123.

Meanwhile, the motion assistance apparatus 1 may include a pair of joint assemblies 12, one disposed on an inner side of the user and the other disposed on an outer side of the user. In the above structure, a knee joint of the user may be more stably supported. In this example, each of the first longitudinal member 122 and the second longitudinal member 123 may be connected to the outer side and the inner side of the user. For example, each of the first longitudinal member 122 and the second longitudinal member 123 may bind rolling cams 121 included in the joint assembly 12 disposed on the outer side of the user and rolling cams 121 included in the joint assembly 12 disposed on the inner side of the user. In the above structure, forces or moments applied to the joint assemblies 12 disposed on the outer side and the inner side of the user, respectively, may be uniformly distributed such that movements of the respective joint assemblies 12 may be synchronized, whereby user inconvenience and resistance may be alleviated. Exemplary structures of the joint assembly 12 will be described with reference to FIGS. 7A through 16.

The second support 13 may support a second portion of the user, and be provided in a shape that encloses the second portion along the outer surface of the user. For example, the second support 13 may be provided to enclose a shank of the user, and provided in a shape including a side corresponding to a contact portion of the user.

The second support 13 may include a connecting frame 131, a second outer side frame 132 disposed on an outer side of the shank, and a second inner side frame 133 disposed on an inner side of the shank. The connecting frame 131 may be configured to connect the second outer side frame 132 and the second inner side frame 133.

The second outer side frame 132 may be fixed to one of the plurality of rolling cams 121 positioned at a terminal end of the joint assembly 12 disposed on the outer side of the user, and the second inner side frame 133 may be fixed to one of the plurality of rolling cams 121 positioned at a terminal end of the joint assembly 12 disposed on the inner side of the user.

Through the connecting frame 131, each of the first longitudinal member 122 and the second longitudinal member 123 may connect the joint assembly 12 disposed on the outer side of the user and the joint assembly 12 disposed on the inner side of the user.

The connecting frame 131 may include a pulley housing 1311, a first pulley 1312, a bearing 1313, a second pulley 1314, and a pulley base 1315.

The pulley housing 1311 may receive the first pulley 1312 and the second pulley 1314. The first longitudinal member 122 and the second longitudinal member 123 may pass through an internal portion of the pulley housing 1311.

The first pulley 1312 may be configured to rotate with respect to the pulley base 1315. A central portion of the first longitudinal member 122 may run over the first pulley 1312. Similarly, the second pulley 1314 may be configured to rotate with respect to the pulley base 1315. A central portion of the second longitudinal member 123 may run over the second pulley 1314. The first pulley 1312 and the second pulley 1314 may reduce friction generated when the first longitudinal member 122 and the second longitudinal member 123 move.

The bearing 1313 may be disposed between the first pulley 1312 and the second pulley 1314, and help the first pulley 1312 and the second pulley 1314 to rotate smoothly. The bearing 1313 may enable the first pulley 1312 and the second pulley 1314 to rotate smoothly even when the first pulley 1312 and the second pulley 1314 rotate in opposite directions or rotate in the same direction at different speeds.

The pulley base 1315 may be disposed in a lower portion of the pulley housing 1311, and support the first pulley 1312, the bearing 1313, and the second pulley 1314.

When the joint assembly 12 performs a flexion motion, the second support 13 may descend with respect to the first support 11. When the joint assembly 12 performs an extension motion, the second support 13 may ascend with respect to the first support 11. That is, the first pulley 1312 and/or the second pulley 1314 rotatably fixed to the second support 13 may function as movable pulleys, and thus increase the force to be transmitted to the second support 13 through the first longitudinal member 122 and/or the second longitudinal member 123. In other words, the first pulley 1312 and/or the second pulley 1314 may function as reducers.

Further, in some example embodiments, the motion assistance apparatus 1 may restrict the maximum extension angle of the joint assembly 12 during extension motion such that the total extension angle between the plurality of rolling cams 121 is restricted not to exceed 180 degrees to reduce a likelihood of (or, alternatively, to prevent) hyperextension of the knee joint of the user.

Figure 7A:
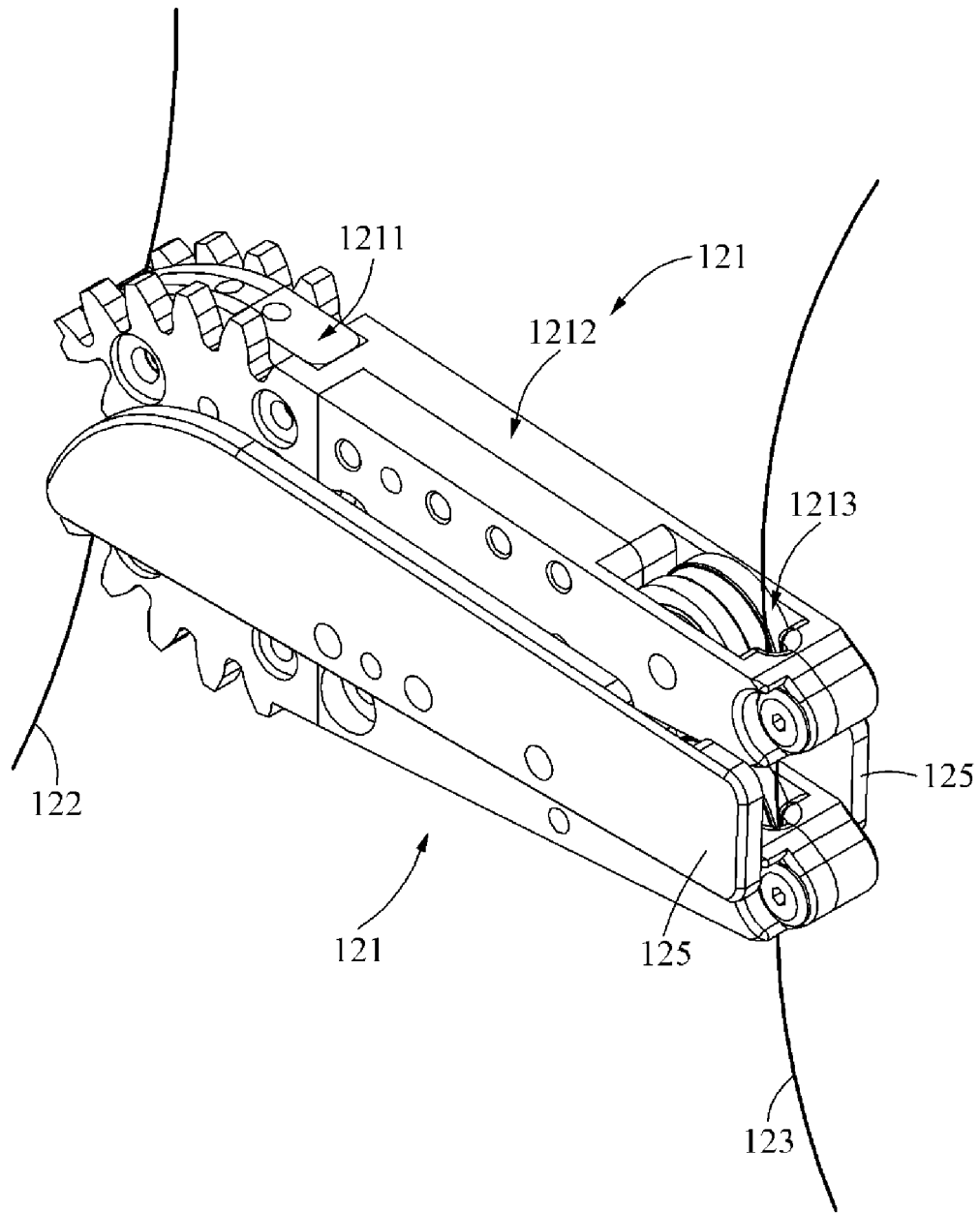
FIG. 7A is a perspective view illustrating a portion of a joint assembly according to at least one example embodiment.
Figure 7B:
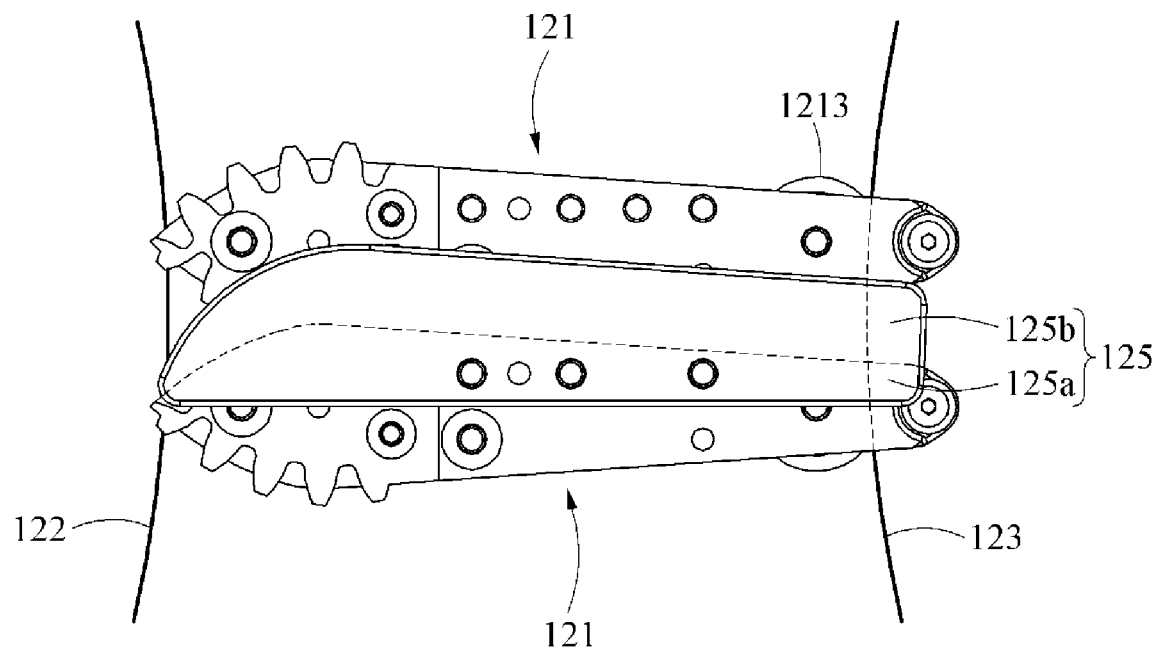
FIG. 7B is a side view illustrating a portion of a joint assembly according to at least one example embodiment.
Figure 8:
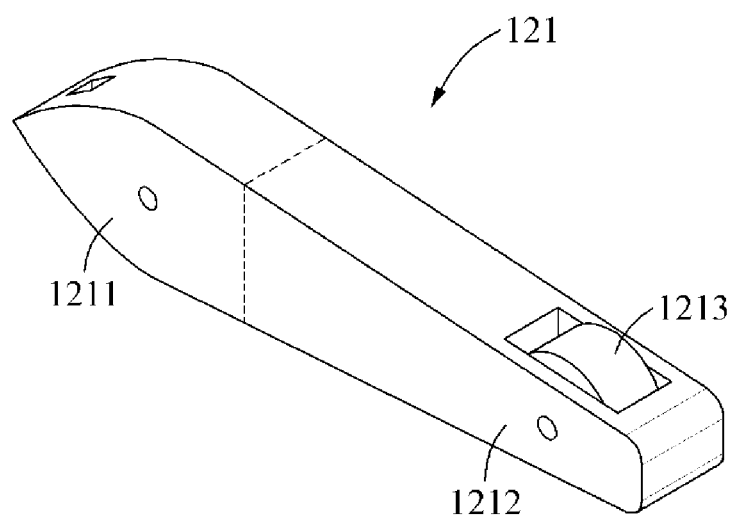
FIG. 8 is a perspective view illustrating a rolling cam according to at least one example embodiment.

FIG. 7A is a perspective view illustrating a portion of a joint assembly according to at least one example embodiment, FIG. 7B is a side view illustrating the portion of the joint assembly according to at least one example embodiment, and FIG. 8 is a perspective view illustrating a rolling cam according to at least one example embodiment.

Referring to FIGS. 7A through 8, the joint assembly 12 may include the plurality of rolling cams 121 and the at least one longitudinal member 122, 123.

A cam may refer to a device with a contour or a groove that performs a rotational motion and/or a reciprocating motion. A rolling cam 121 may move relative to another adjacent rolling cam 121 while performing a rolling contact movement with the adjacent rolling cam 121. The rolling cam 121 may include a cam portion 1211, an extension 1212, and a rotary member 1213.

The cam portion 1211 may include a portion to be in contact with adjacent rolling cams 121. The adjacent rolling cams 121 may perform a rolling contact movement along at least a portion of an edge of the cam portion 1211.

The extension 1212 may extend from the cam portion 1211. For example, a width of the extension 1212 may decrease in a direction away from the cam portion 1211. In this example, when cam portions 1211 of the adjacent rolling cams 121 perform rolling contact movements, adjacent extensions 1212 may touch each other due to manufacturing errors of the rolling cams 121 such that the cam portions 1211 may not perform the rolling contact movements appropriately. In the above structure, such an issue may be less likely (or, alternatively, prevented) due to the decreased width of the extension 1212.

The rotary member 1213 may be rotatably provided in the extension 1212, and rotate while being in contact with the longitudinal member 123. For example, the rotary member 1213 may be exposed outside of the extension 1212. That is, the rotary member 1213 may have a diameter greater than the width of the extension 1212 at a position at which the rotary member 1213 is provided in the extension 1212. In this example, a durability of the longitudinal member 123 to be in contact with the rotary member 1213 may improve. Further, a path along which the longitudinal member 123 moves may have a curved shape, and thus the longitudinal member 123 may move smoothly.

The joint assembly 12 may further include a rolling cam guide 125. The rolling cam guide 125 may cover at least a portion of sides of the rolling cams 121. For example, the rolling cam guide 125 may include a fixed portion 125a to be fixed to a side of one rolling cam 121, and a guide portion 125b extending from the fixed portion 125a and overlaying at least a portion of a side of another rolling cam 121.

Meanwhile, in another example, the rolling cam guide 125 may be fixed to one of the first support 11 and the second support 13 of FIG. 2, and have a shape extending from the one support toward the other support, thereby being disposed on the sides of the plurality of rolling cams 121. Through the above structure, mutual separation of the rolling cams 121 may be less likely (or, alternatively, prevented).

One end and another end of the at least one longitudinal member 122, 123 may each be connected to the rotor 112 of FIG. 2. The longitudinal member 122, 123 may move in a longitudinal direction to control the plurality of rolling cams 121. For example, the longitudinal member 122, 123 may be a wire, a cable, a string, a rubber band, a spring, a belt, or a chain. However, example embodiments are not limited thereto.

The longitudinal member 122, 123 may be a plurality of longitudinal members, for example, the first longitudinal member 122 that passes through cam portions 1211 of the adjacent rolling cams 121, and the second longitudinal member 123 that passes through extensions 1212 of the adjacent rolling cams 121. When the first longitudinal member 122 is pulled toward the rotor 112 of FIG. 2, the second longitudinal member 123 may be released in a direction away from the rotor 112. That is, the first longitudinal member 122 may perform the flexion function of the joint assembly 12. In this example, the adjacent cam portions 1211 may perform rolling contact movements with each other, and the adjacent extensions 1212 may be spaced apart from each other, whereby the knee joint of the user may perform a flexion motion. Conversely, when the second longitudinal member 123 is pulled toward the rotor 112, the first longitudinal member 122 may be released in a direction away from the rotor 112. That is, the second longitudinal member 123 may perform the extension function of the joint assembly 12.

The first longitudinal member 122 and the second longitudinal member 123 may bind the rolling cams 121 while forming a desired (or, alternatively, a predetermined) path based on a torque applied to the rotor 112. The joint assembly 12 may include the plurality of rolling cams 121 that each perform a rolling contact movement with respect to another adjacent rolling cam 121, and thus may have a plurality of degrees of freedom. Thus, when a desired (or, alternatively, a predetermined) tensile force is applied to the first longitudinal member 122 and the second longitudinal member 123, the joint assembly 12 may change its shape to minimize an internal stress applied to the plurality of rolling cams 121 based on the tensile force. In the above structure, when a power, for example, a torque, is transmitted from the rotor 112 to the first longitudinal member 122 and the second longitudinal member 123, a loss of the power may be reduced.

The motion assistance apparatus 1 may include and/or be configured to communicate with a controller and one or more sensors (not shown).

The one or more sensors may include one or more of pressure sensors, a potentiometer, a gyrosensor, an accelerometer an electromyography (EMG) sensor, and the like.

The controller may include a memory and processing circuitry.

The memory may include may include a non-transitory computer readable medium. Examples of non-transitory computer-readable media include magnetic media such as hard disks, floppy disks, and magnetic tape; optical media such as CD ROM discs and DVDs; magneto-optical media such as optical discs; and hardware devices that are specially configured to store and perform program instructions, such as read-only memory (ROM), random access memory (RAM), flash memory, and the like. The non-transitory computer-readable media may also be a distributed network, so that the program instructions are stored and executed in a distributed fashion.

The processing circuitry may include a processor, Central Processing Unit (CPU), a controller, an arithmetic logic unit (ALU), a digital signal processor, a microcomputer, a field programmable gate array (FPGA), an Application Specific Integrated Circuit (ASIC), a System-on-Chip (SoC), a programmable logic unit, a microprocessor, or any other device capable of performing operations in a defined manner.

The processing circuitry may be configured, through a layout design and/or execution of computer readable instructions stored in the memory, as a special purpose computer to control the rotor 112 based on signals received from the one or more sensors. For example, the controller may determine a current phase of the gait cycle based on the signals, may determine whether the user is performing a flexion motion or an extension motion of, for example, their knees based on the current phase of the gait cycle.

In some example embodiments, controller may instruct the rotor 112 to rotate in a first direction to pull the first longitudinal member 122 toward the rotor 112, if the controller determines that user is performing flexion motion, and rotate in a second direction to pull the second longitudinal member 123 toward the rotor 112, if the controller determines that user is performing extension motion.

In some other example embodiments, the controller may determine whether the user is attempting to sit down or stand up based on the signals, and control the rotor 112 to rotate in the first direction, if the controller determines that the user is attempting to sit down and rotate in the second direction, if the controller determines that the user is attempting to stand up.

Meanwhile, in the joint assembly 12, a shape of the cam portions 1211 of the rolling cam 121 has various aspects. When the cam portions 1211 of the rolling cam 121 perform rolling contact movements, the flexion motion or extension motion of the joint assembly 12 may be performed linearly. Thus, a torque may be transmitted accurately between the first support 11 and the second support 13 through the joint assembly 12. Further, as the tensile force applied to the first longitudinal member 122 or the second longitudinal member 123 increases, a normal force applied by the second longitudinal member 123 in a longitudinal direction of the extension 1212 may increase, and thus a frictional force generated between the extension 1212 of the rolling cam 121 and the second longitudinal member 123 may increase. In this example, the rolling cam 121 may have a difficulty in moving in freedom. Hereinafter, a method of determining a shape of the rolling cam 121 to enable the rolling cam 121 to move more smoothly and to implement a linear motion and accurate torque transmission through the joint assembly 12 will be described.

Figure 9:
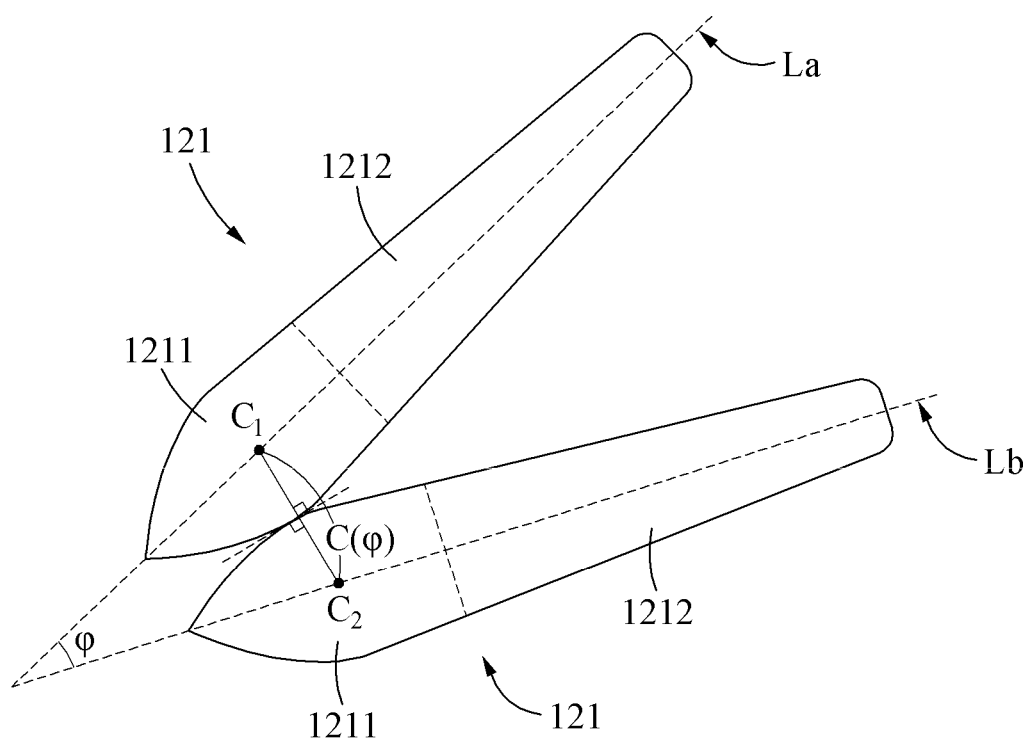
FIG. 9 illustrates respective center lines of adjacent rolling cams, and an angle between the center lines according to at least one example embodiment.
Figure 10:
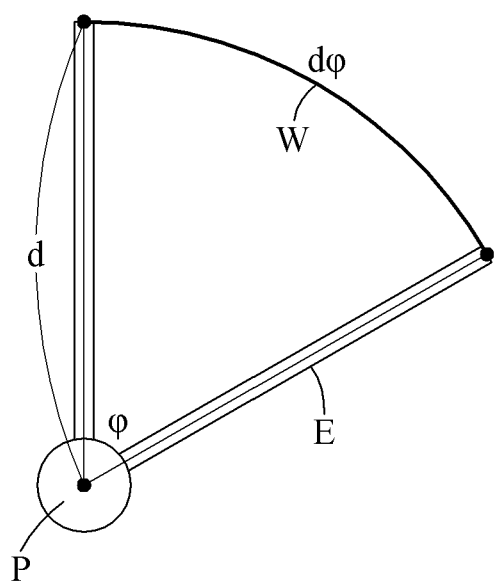
FIG. 10 illustrates a basic concept for determining shapes of rolling cams according to at least one example embodiment, that is, a mathematical representation of a joint assembly including a single joint and an extension extending from the joint.
Figure 11:
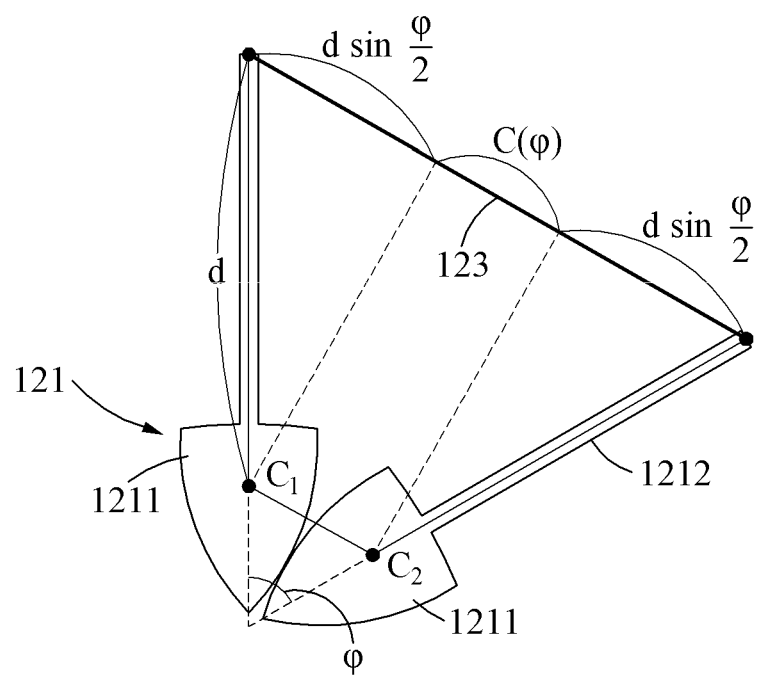
FIG. 11 illustrates a mathematical representation of a joint assembly according to at least one example embodiment.
Figure 12:
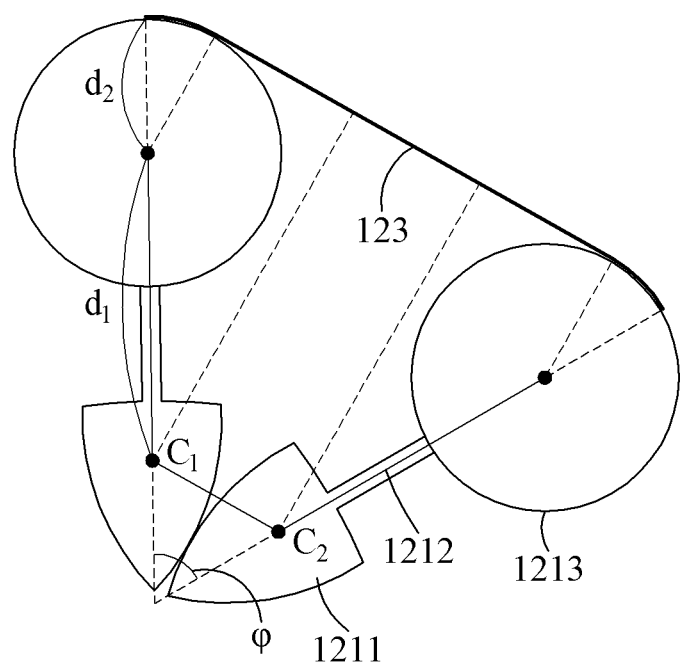
FIG. 12 illustrates a mathematical representation of a joint assembly according to at least one example embodiment.
Figure 13:
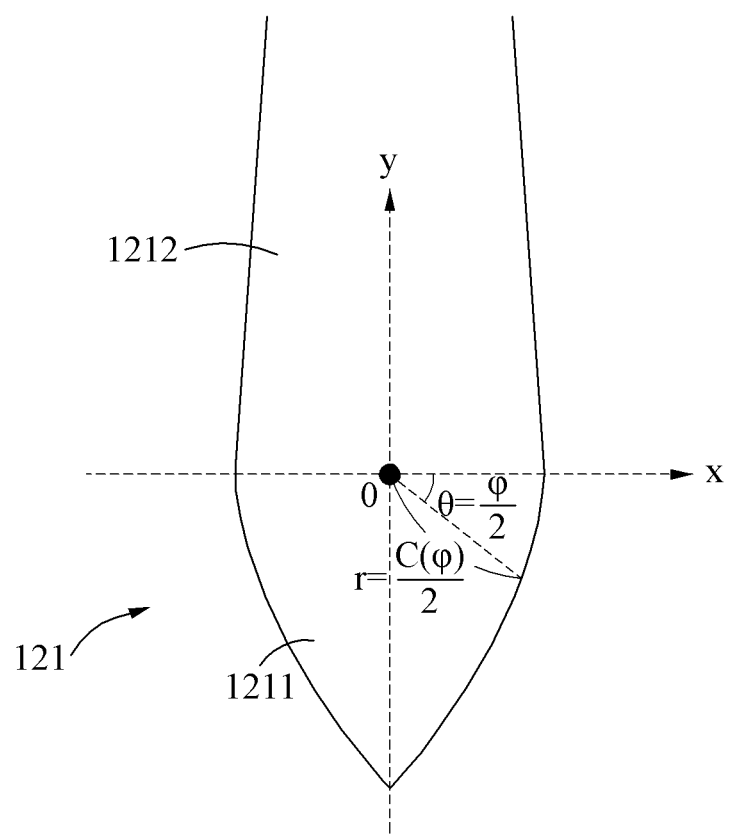
FIG. 13 illustrates a method of determining an edge shape of a cam portion according to at least one example embodiment.

FIG. 9 illustrates respective center lines of adjacent rolling cams, and an angle between the center lines according to at least one example embodiment. FIG. 10 illustrates a basic concept for determining shapes of rolling cams according to at least one example embodiment, that is, a mathematical representation of a joint assembly including a single joint and an extension extending from the joint, and FIGS. 11 and 12 illustrate mathematical representations of the joint assembly according to at least one example embodiment. FIG. 13 illustrates a method of determining an edge shape of a cam portion according to at least one example embodiment.

Referring to FIG. 9, two adjacent rolling cams 121 of the joint assembly 12 may have shapes symmetrical in a lateral direction with respect to a first virtual center line La and a second virtual center line Lb, respectively. In a case in which the two adjacent cam portions 1211 perform rolling contact movements, a cam distance $C(\varphi)$ between the first virtual center line La and the second virtual center line Lb measured in a direction orthogonal to a tangent line at a point at which the two adjacent cam portions 1211 are in contact with each other may change in response to a change in a cam angle $\varphi$ between the first virtual center line La and the second virtual center line Lb.

Meanwhile, when using a condition that the adjacent cam portions 1211 perform rolling contact movements, an edge shape of the cam portion 1211 may be deduced as expressed by Equation 1, as polar coordinates of (r, θ).

$$r = \frac{C(\phi)}{2}, \theta = \frac{\phi}{2} \quad \text{[Equation 1]}$$

In Equation 1, r denotes a distance from the origin O of a rectangular coordinate system (x, y) to a desired (or, alternatively, a predetermined) point on an edge of the cam portion 1211 when the first virtual center line La or the second virtual center line Lb of the cam portion 1211 is disposed on an axis y of the rectangular coordinate system (x, y). θ denotes an angle measured in a clockwise direction (or counterclockwise direction) from a positive direction (or negative direction) of an axis x to a virtual line connecting the origin O and the point on the edge of the cam portion 1211.

Meanwhile, according to the above method of determining the shape of the cam portion 1211, all perpendicular lines of tangent lines drawn at the points on the edge of the portion to be in contact with the adjacent cam portions 1211 may intersect at the origin O as shown in FIG. 13. The origin O may be defined as a "cam center $C_1$, $C_2$". In this example, the cam distance C(φ) may be construed as a distance between respective cam centers $C_1$ and $C_2$ of the two adjacent cam portions 1211. That is, the cam distance C(φ) may change based on the cam angle φ between the adjacent rolling cams 121.

Based on the above-defined terminologies, the shape of the rolling cam 121 will be described with reference to FIG. 10.

While an extension E that rotates about a single point, that is, a joint P, moves a desired (or, alternatively, a predetermined) angle φ, an end portion of the extension E may be defined based on the angle φ and a length d of the extension E and move along a path corresponding to an arc with a length of dφ. Thus, under the assumption that a second longitudinal member W maintains a shape of the arc while the extension E rotates, a frictional force generated between the extension E and the second longitudinal member W may be zero in theory, and thus the extension E may rotate in freedom. Similarly, in a case in which an angle between two adjacent extensions E corresponds to φ, and a length of the second longitudinal member W connecting the two extensions E corresponds to dφ which is the length of the arc corresponding to the angle φ, the extensions E may rotate smoothly as if rotating along the arc.

Meanwhile, as shown in FIG. 11, when a tensile force is applied to the second longitudinal member 123 in reality, the second longitudinal member 123 may connect adjacent rolling cams 121 with a straight line corresponding to a shortest path, and the cam centers $C_1$ and $C_2$ of the adjacent rolling cams 121 may be spaced apart from each other by the cam distance C(φ) corresponding to the cam angle φ. Thus, to apply the basic concept as shown in FIG. 9, by designing a length of the straight line connecting the adjacent extensions 1212 to be equal to a sum of the length dφ of the arc corresponding to the cam angle φ and an initial value C0 of the cam distance C(φ), the extensions 1212 may rotate smoothly as if rotating along the arc, which may be expressed as given by Equation 2.

$$C(\varphi) = d\varphi - 2d \sin(\varphi/2) + C0 \quad \text{[Equation 2]}$$

In Equation 2, α denotes a desired (or, alternatively, a predetermined) cam angle between adjacent rolling cams 121. d denotes a distance from the cam center $C_1$, $C_2$ to a point of the extension 1212 connected to the longitudinal member 123. C0 denotes a distance between adjacent cam centers $C_1$ and $C_2$ when the cam angle φ is 0 degrees.

Further, according to the above conditions, a value obtained by subtracting the initial value C0 corresponding to a constant from a linear distance between the two adjacent extensions 1212 is proportional to the cam angle φ or a variance Δφ in the cam angle φ. Similarly, when the respective rolling cams 121 are designed under the above conditions, a flexion motion or extension motion of the joint assembly 12 including such rolling cams 121 may be performed linearly.

Meanwhile, if a variance in an angle between a pair of adjacent rolling cams 121, among the plurality of rolling cams 121, corresponds to +Δφ while a length of the first longitudinal member 122 and a length of the second longitudinal member 123 respectively connected to two rolling cams 121 positioned at both ends of the joint assembly 12 are maintained, the rolling cams 121 may rotate smoothly such that a sum of variances in angles of other pairs of adjacent rolling cams 121 may correspond to −Δφ. Thus, the overall angle between the two rolling cams 121 positioned at both ends of the joint assembly 12 may remain the same. That is, each rolling cam 121 may rotate smoothly, and a variance in an angel between adjacent two rolling cams 121 may be offset as remaining rolling cams 121 rotate smoothly. Thus, each rolling cam 121 may maintain the overall angle of the joint assembly 12 and also be self-aligned in compliance with an external force applied to the joint assembly 12, whereby the user wearability may improve. Meanwhile, in a case in which an external force is not applied, each rolling cam 121 may maintain the overall angle of the joint assembly 12, and also be self-aligned to reduce (or, alternatively, minimize) an internal stress of the joint assembly 12, whereby a durability of the joint assembly 12 may improve.

Hereinafter, a case in which the rolling cam 121 of the joint assembly 12 includes the rotary member 1213 as shown in FIG. 12 will be described. A portion of the second longitudinal member 123 may be connected to one end of extensions 1212 through the rotary member 1213. When a length of an extension 1212 is defined as d1 and a radius of the rotary member 1213 is defined as d2, cam shapes of adjacent cam portions 1211 may be expressed by Equation 3.

$$C(\varphi) = (d1+d2)\varphi - d2\varphi - 2d1 \sin(\varphi/2) + C0 \quad \text{[Equation 3]}$$

Equation 3 may be arranged as expressed by Equation 4.

$$C(\varphi) = d1\varphi - 2d1 \sin(\varphi/2) + C0 \quad \text{[Equation 4]}$$

The basic concept provided above may be applicable to various example embodiments. Meanwhile, the above description is merely a single example of the method of determining the edge shape of the cam portion 1211, and thus example embodiments are not limited thereto.

Figure 14:
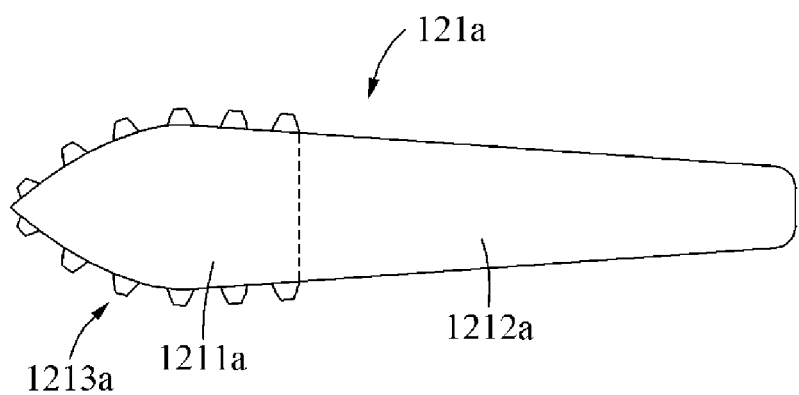
FIG. 14 is a side view illustrating a rolling cam according to at least one example embodiment.

FIG. 14 is a side view illustrating a rolling cam according to at least one example embodiment.

Referring to FIG. 14, a rolling cam 121a may include a cam portion 1211a, an extension 1212a, and a slip preventer (or, alternatively, a slip reducer) 1213a configured to reduce a probability of (or, alternatively, prevent) slip of adjacent cam portions 1211a. The slip preventer 1213a may have, for example, a gear tooth shape provided on an edge of the cam portion 1211a.

Figure 15:
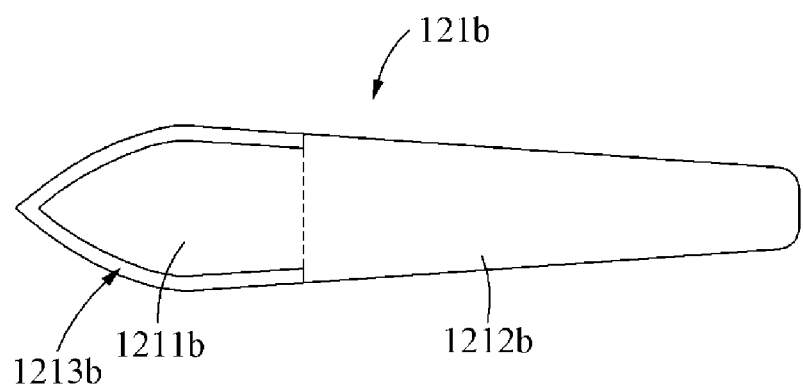
FIG. 15 is a side view illustrating a rolling cam according to at least one example embodiment.

FIG. 15 is a side view illustrating a rolling cam according to at least one example embodiment.

Referring to FIG. 15, a rolling cam 121b may include a cam portion 1211b, an extension 1212b, and a slip preventer 1213b. The slip preventer 1213b may include, for example, a friction pad provided on an edge of the cam portion 1211b. A material of the friction pad may be, for example, rubber or polyurethane.

Figure 16:
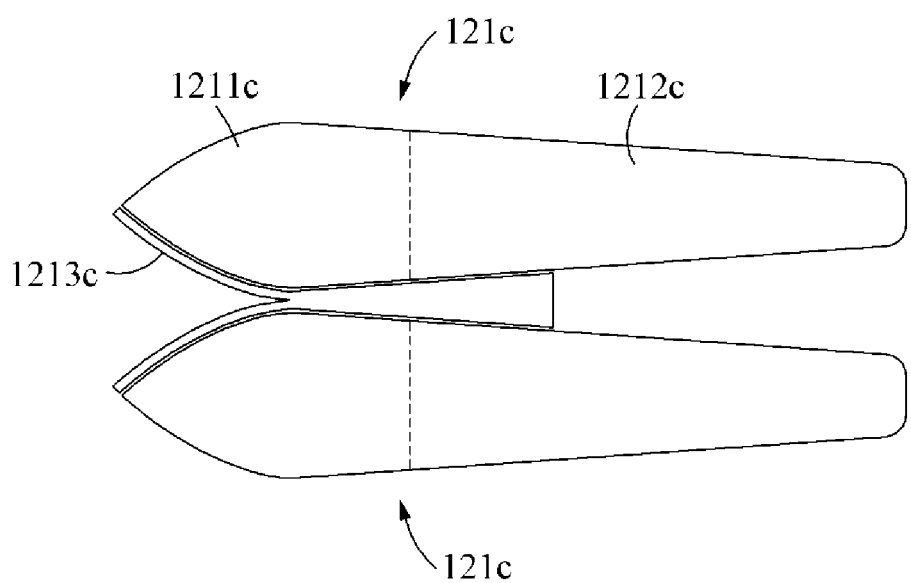
FIG. 16 is a side view illustrating a joint assembly according to at least one example embodiment.

FIG. 16 is a side view illustrating a joint assembly according to at least one example embodiment.

Referring to FIG. 16, a joint assembly 12c may include a plurality of rolling cams 121c, and a slip preventer 1213c disposed between adjacent rolling cams 121c. The slip preventer 1213c may be, for example, a flat spring attached to each of the adjacent rolling cams 121c.

Figure 17:
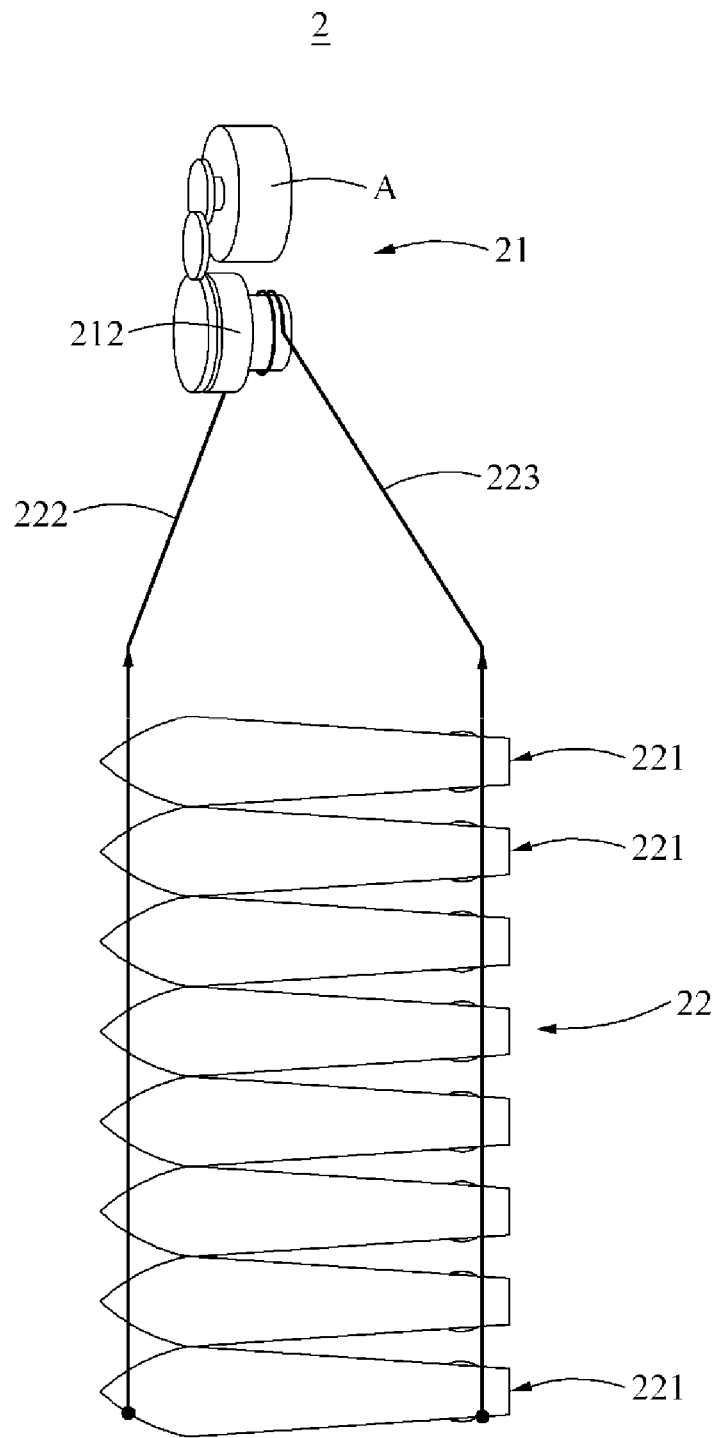
FIG. 17 illustrates a motion assistance apparatus according to at least one example embodiment.

FIG. 17 illustrates a motion assistance apparatus according to at least one example embodiment.

Referring to FIG. 17, a motion assistance apparatus 2 may include a first support 21 including a rotor 212, a joint assembly 22 including a plurality of rolling cams 221, a first longitudinal member 222, and a second longitudinal member 223, and an actuator A configured to actuate the rotor 212.

One end of the first longitudinal member 222 may be fixed to the rotor 212, and another end thereof may be fixed to a cam portion of a last rolling cam 221 of the joint assembly 22. One end of the second longitudinal member 223 may be fixed to the rotor 212, and another end thereof may be fixed to an extension of the last rolling cam 221 of the joint assembly 22. By the above shape, a motion of a joint of a user may be assisted using only a single joint assembly 22 disposed on an inner side or outer side of the user. Thus, the configuration of the motion assistance apparatus 2 may be simplified, and the motion assistance apparatus 2 may be miniaturized.

Figure 18:
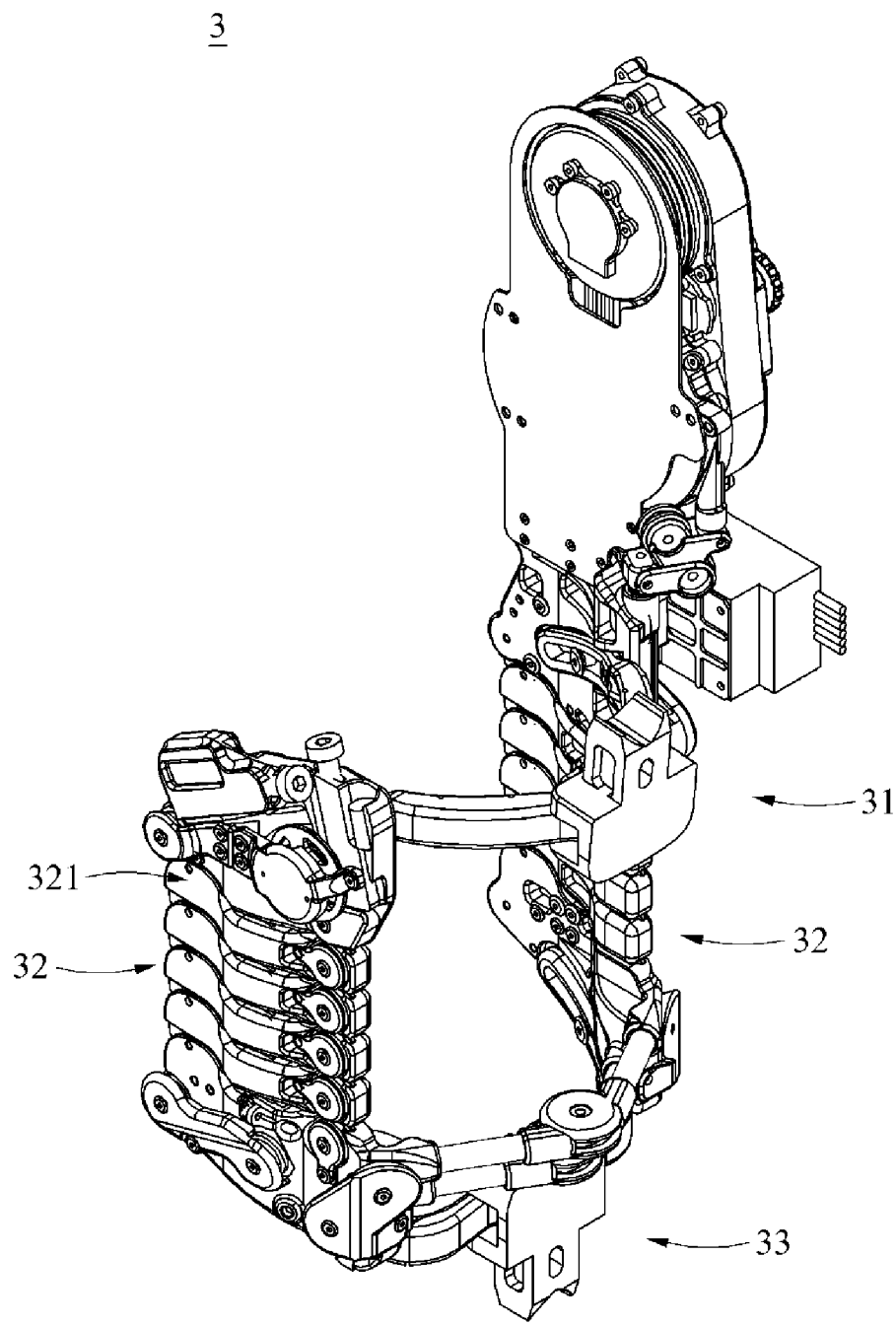
FIG. 18 is a perspective view illustrating a motion assistance apparatus according to at least one example embodiment.
Figure 19:
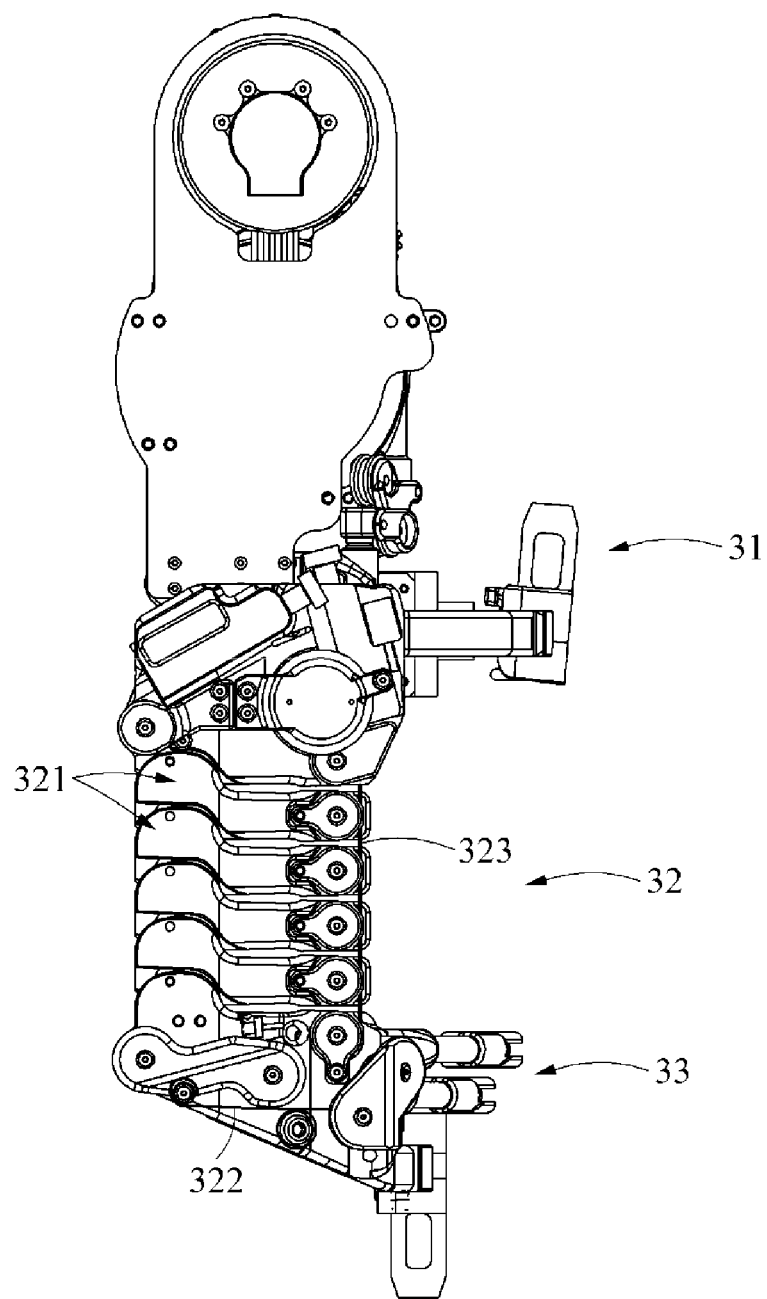
FIG. 19 is a side view illustrating a motion assistance apparatus according to at least one example embodiment.
Figure 20:
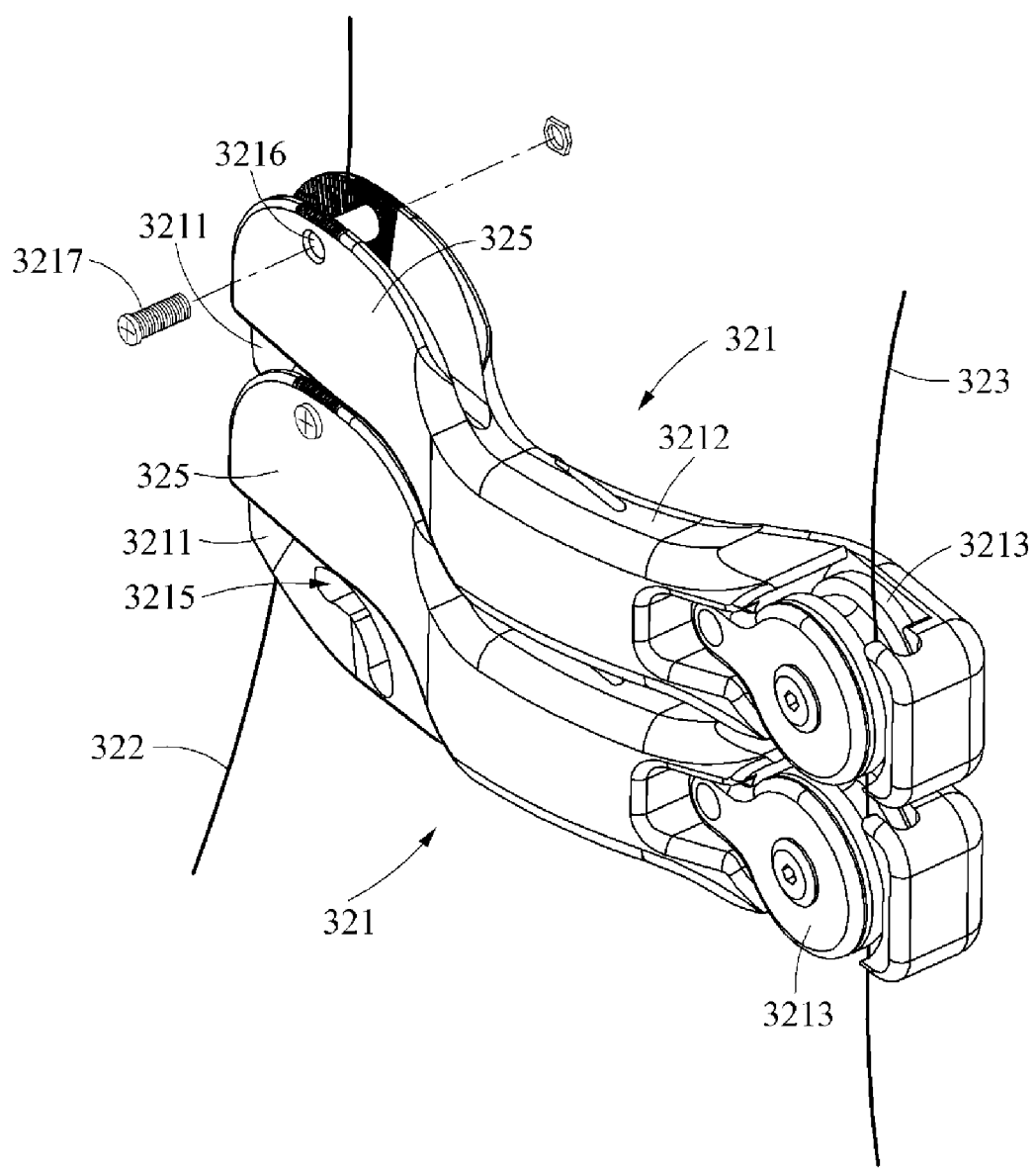
FIG. 20 is a perspective view illustrating a joint assembly according to at least one example embodiment.

FIG. 18 is a perspective view illustrating a motion assistance apparatus according to at least one example embodiment, FIG. 19 is a side view illustrating the motion assistance apparatus according to at least one example embodiment, and FIG. 20 is a perspective view illustrating a joint assembly according to at least one example embodiment.

Referring to FIGS. 18 through 20, a motion assistance apparatus 3 may include a first support 31, a joint assembly 32, and a second support 33. The joint assembly 32 may include a plurality of rolling cams 321, a first longitudinal member 322, a second longitudinal member 323, and a rolling cam guide 325.

A rolling cam 321 may include a cam portion 3211, an extension 3212, a rotary member 3213, a cam path 3215, a coupling hole 3216, and a fastening member 3217.

The rolling cam guide 325 may extend from a side of one of the rolling cams 321, and overlap at least a portion of a side of another adjacent rolling cam 321. For example, the rolling cam guide 325 may have a shape extending from both sides of one of the cam portions 3211 toward another adjacent cam portion 3211. The rolling cam guide 325 may be construed as corresponding to the guide portion 125b of the rolling cam guide 125 of FIG. 7A and the like. At least two of the cam portion 3211, the extension 3212, and the rolling cam guide 325 may be provided, for example, as an integral body.

The cam path 3215 may be formed to correspond to a rolling contact path of adjacent rolling cams 321. One of the cam path 3215 and the coupling hole 3216 may be formed in the cam portion 3211, and the other of the cam path 3215 and the coupling hole 3216 may be formed in the rolling cam guide 325. The fastening member 3217 may be fastened to penetrate through the cam path 3215 and the coupling hole 3216. The above structure may more definitely reduce (or, alternatively, prevent) separation between adjacent rolling cams 321 while allowing the adjacent rolling cams 321 to perform rolling contact movements through predetermined shapes.

While example embodiments have described the motion assistance apparatus in terms of an apparatus that assists the flexion and extension motion of the knee joints of the user, example embodiments are not limited thereto. For example, in some example embodiments, the motion assistance apparatus may assist a motion of an ankle joint. For example, the first support 11 may support a front side of a shin of the user, the second support 13 may support a sole of the user, and the joint assembly 12 may assist in motion of the ankle joint of the user. The joint assembly 12 may include a plurality of cams to assist the ankle joint of the user in performing eversion motion to bend outwards and inversion motion to bend inwards such that, while an axes of rotation of the ankle may change during the aforementioned motions, the joint assembly 12 may adjust the distance between the plurality of cams to self-aligns in compliance therewith, and, thus, whereby the user wearability may improve.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A joint assembly, comprising:
a first rolling cam including a first cam portion, and a first extension, the first extension extending from the first cam portion;
a second rolling cam including a second cam portion and a second extension, the second cam portion configured to contact the first cam portion, and the second extension extending from the second cam portion;
a first longitudinal member connecting the first cam portion and the second cam portion; and
a second longitudinal member connecting the first extension and the second extension,
wherein the first rolling cam and the second rolling cam performs a rolling contact movement along at least a portion of an edge of each cam portion.

2. The joint assembly of claim 1, wherein
the first cam portion has a shape symmetrical in a lateral direction with respect to a first virtual center line, and
the second cam portion has a shape symmetrical in a lateral direction with respect to a second virtual center line.

3. The joint assembly of claim 2, wherein an edge shape of the first cam portion and an edge shape of the second cam portion satisfy Equation 1 and Equation 2, respectively, $$r1 = \frac{C(\varphi)}{2}, \theta1 = \frac{\phi}{2}$$ [Equation 1]

-continued $$r2 = \frac{C(\varphi)}{2}, \theta2 = \frac{\phi}{2},$$ [Equation 2]

wherein φ denotes an angle between the first virtual center line and the second virtual center line, C(φ) denotes a distance between the first virtual center line and the second virtual center line in a direction orthogonal to a tangent line at a point at which the first cam portion is in contact with the second cam portion, r1 denotes a distance from a first intersection point to a point on an edge of the first cam portion, the first intersection point being a point at which the first virtual center line and a first orthogonal virtual line orthogonal thereto meet, θ1 denotes an angle measured in a clockwise direction from a positive direction of the first orthogonal virtual line to a virtual line connecting the first intersection point and the point on the edge of the first cam portion, r2 denotes a distance from a second intersection point to a point on an edge of the second cam portion, the second intersection point being a portion at which the second virtual center line and a second orthogonal virtual line orthogonal thereto meet, and θ2 denotes an angle measured in a counterclockwise direction from a negative of the second orthogonal virtual line to a virtual line connecting the second intersection point and the point on the edge of the second cam portion.

4. The joint assembly of claim 1, wherein a width of the first extension decreases in a direction away from the first cam portion.

5. The joint assembly of claim 4, wherein the first rolling cam further comprises:
a rotary member associated with the first extension, the rotary member configured to rotate.

6. The joint assembly of claim 5, wherein
the rotary member is exposed outside of the first extension.

7. The joint assembly of claim 1, further comprising:
a rolling cam guide configured to cover at least a portion of a side of the first rolling cam and at least a portion of a side of the second rolling cam.

8. The joint assembly of claim 1, further comprising:
a rolling cam guide including a fixed portion and a guide portion, the fixed portion configured to attach to a side of the first rolling cam, and the guide portion extending from the fixed portion and overlapping at least a portion of a side of the second rolling cam.

9. The joint assembly of claim 1, further comprising:
a slip reducer between the first cam portion and the second cam portion.

10. The joint assembly of claim 1, further comprising:
an elastic member between the first rolling cam and the second rolling cam.

11. The joint assembly of claim 1, wherein
a sum of a product of an angle φ and a distance d and an initial distance C0 is equal to a length of a portion between a point of the first extension connected to the second longitudinal member and a point of the second extension connected to the second longitudinal member,
the angle φ is an angle between the first rolling cam and the second rolling cam,
the distance d is a distance from a cam center of the second cam portion to the point of the second extension connected to the second longitudinal member, and
the initial distance C0 is a distance between a cam center of the first cam portion and the cam center of the second cam portion when the angle φ corresponds to 0 degrees.

12. A motion assistance apparatus, comprising:
a first support configured to support a first portion of a user;
a second support configured to support a second portion of the user; and
a first joint assembly including a plurality of first rolling cams and at least one longitudinal member configured to bind the plurality of first rolling cams, the plurality of first rolling cams being between the first support and the second support, each of the plurality of first rolling cams including a cam portion and an extension extending from the cam portion, and the at least one longitudinal member including a first longitudinal member and a second longitudinal member, the first longitudinal member connected to the cam portion of each of the plurality of first rolling cams, and the second longitudinal member connected to the extension of each of the plurality of first rolling cams,
wherein the plurality of first rolling cams performs a rolling contact movement along at least a portion of an edge of each cam portion.

13. The motion assistance apparatus of claim 12, further comprising:
a second joint assembly including a plurality of second rolling cams configured to connect the first support and the second support, wherein
the first joint assembly is configured to attach to an outer side of the user, and the second joint assembly is configured to attach to an inner side of the user.

14. The motion assistance apparatus of claim 13, further comprising:
a first pulley configured to rotate with respect to the second support, the first pulley configured to hold a central portion of the first longitudinal member, the first longitudinal member being connected to the outer side of the user and the inner side of the user.

15. The motion assistance apparatus of claim 14, further comprising:
a second pulley configured to rotate with respect to the second support, the second pulley configured to hold a central portion of the second longitudinal member, the second longitudinal member being connected to the outer side of the user and the inner side of the user.

16. The motion assistance apparatus of claim 13, wherein the first support comprises:
a first supporting frame configured to enclose the first portion of the user; and
a rotor configured to rotate with respect to the first supporting frame, the rotor configured to connect to a first end portion of the first longitudinal member and a first end portion of the second longitudinal member.

17. The motion assistance apparatus of claim 16, wherein the rotor comprises:
a rotor body configured to rotate with respect to the first support; and
a tensile force adjuster movably provided in the rotor body, the tensile force adjuster configured to connect to one end of one of the first longitudinal member and the second longitudinal member.

18. The motion assistance apparatus of claim 16, further comprising:

a slack reducing elastic body connected to a second end portion of the first longitudinal member and a second end portion of the second longitudinal member.

* * * * *